US00PP17940P2

(12) United States Plant Patent
Hanes

(10) Patent No.: US PP17,940 P2
(45) Date of Patent: Aug. 21, 2007

(54) *PETUNIA* PLANT NAMED 'JAM BULE'

(50) Latin Name: ***Petunia* sp.**
Varietal Denomination: Jam Bule

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,366

(22) Filed: Mar. 7, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by medium to large, deep-blue flowers, medium-green foliage with elliptical leaves, a medium, round, bushy, moderately tight plant habit with moderately vigorous growth, an initially low, spreading and creeping to trailing plant habit with an early and continuous flowering response, is disclosed.

1 Drawing Sheet

Genus and species: *Petunia* sp.
Variety denomination: 'Jam Bule'.

BACKGROUND OF THE NEW PLANT

The present invention comprises a new and distinct cultivar of *petunia,* botanically known as a *Petunia* sp., and hereinafter referred to by the cultivar name 'Jam Bule'. The new cultivar originated from a hybridization made in February 2002 in Gilroy, Calif. The female parent was 'Kakegawa S28' (U.S. Plant Pat. No. 13,887, also known as 'Supertunia Royal Velvet'), a purple-flowered commercial *petunia* plant (unpatented), while the male parent was 'PY152', a blue-flowered proprietary *petunia* plant (unpatented).

The new cultivar was created in 2002 in Gilroy, Calif. and has been asexually reproduced repeatedly by vegetative cuttings and tissue culture in Gilroy, Calif., and Andijk, The Netherlands over a two-year period. The plant has also been trialed at Gilroy, Calif. and Andijk, The Netherlands. The present invention has been found to retain its distinctive characteristics through successive asexual propagations.

Plant Breeder's Rights for this cultivar were applied for in Canada on Mar. 29, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium to large deep-blue flowers;
2. Medium-green foliage with elliptical leaves;
3. A medium sized, rounded, bushy and moderately tight plant habit;
4. Moderately vigorous growth;
5. An initially low, spreading and creeping to trailing plant habit; and 6. An early and continuous flowering response.

DESCRIPTION OF PHOTOGRAPH

This new *petunia* plant is illustrated by the accompanying photograph which shows the overall plant habit including blooms, buds, and foliage of the plant; the colors shown are as true as can be reasonably obtained by conventional photographic procedures. The photograph is of a 3-month-old plant grown in a greenhouse in Hillscheid, Germany.

DESCRIPTION OF THE NEW CULTIVAR

The following detailed description sets forth the distinctive characteristics of 'Jam Bule'. The data which define these characteristics were collected from asexual reproductions carried out in Hillscheid, Germany. The plant history was taken on 5 to 6-week old plants which were planted as rooted cuttings in 12-cm pots in early July 2005 and grown in a greenhouse. The plants were pinched once. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
*Family.*—Solanaceae.
*Botanical.*—*Petunia* sp.
*Common name.*—*Petunia.*

Parentage:
*Female parent.*—'Kakegawa S28' a commercial purple-flowered *petunia* plant (U.S. Plant Pat. No. 13,887).
*Male parent.*—'PY152', a proprietary *petunia* plant having blue flowers (unpatented).

Growth:
*Form.*—Herbaceous annual.

*Habit.*—Spreading initially low or decumbent to trailing plant habit with fair branching.

*Height* (*measured from the top of the soil*).—9.8 cm.

*Width* (*horizontal plant diameter*).—27.7 cm.

*Propagation.*—Terminal tips for cutting.

*Time to produce a finished flowering plant.*—About 10 weeks for a 12-cm pot in the Spring.

*Outdoor plant performance.*—Use in hanging baskets and containers.

*Time to initiate and develop roots.*—About 25 days.

*Root description.*—Fibrous, self-branching.

Stems:

*Average number* (*basal*).—4.5.

*Length of basal branches* (*from the base of the stem to the tip*).—21.8 cm.

*Internode length.*—4.3 cm.

*Diameter of branches* (*from midpoint*).—0.4 cm.

*Stem color.*—RHS 143A to RHS 143B (green).

*Anthocyanin.*—Absent.

*Texture.*—Densely pubescent.

Leaves:

*Arrangement.*—Initially alternate and later appears mostly opposite in pairs; partly appearing decussate.

*Size.*—Length: 6.7 cm. Width: 4.2 cm.

*Shape.*—Elliptical.

*Margin.*—Entire.

*Apex.*—Acute to obtuse.

*Base.*—Attenuate.

*Color.*—Upper surface: RHS 137B (green). Lower surface: Between RHS 137D to RHS 143A.

*Texture.*—Upper surface: Velvety with short pubescence. Lower surface: Dense hair along the leaf veins and margins.

*Venation.*—Mainly pinnate.

*Venation color.*—RHS 144C.

*Petioles.*—General: Not always clearly distinct from the base of the leaf. Length: Up to 0.3 cm. Width: 0.3 cm. Color: Upper surface: RHS 144C. Lower surface: RHS 144D. Texture: Densely pubescent, especially along the midrib.

Flower bud:

*Shape.*—Tube-shaped with furrows.

*Size.*—Length: 3.8 cm. Diameter: 1.2 cm.

*Color at tight bud.*—RHS N92D (dull deep-violet) to RHS N92B at the tip.

*Immature flower color.*—RHS N92B.

Inflorescence:

*Blooming habit.*—Continuous from Spring to Fall.

*Inflorescence type.*—Flowers appear solitary on pedicels, emerging singularly at the nodes.

*Number of flowers per node.*—1.

*Lastingness of individual blooms on the plant.*—6 to 7 days.

*Fragrance.*—Weak, *petunia*-like.

*Pedicels.*—Color: RHS 143B (light-green). Length: 5.9 cm. Diameter: About 0.2 cm. Texture: Densely pubescent.

Flowers:

*Shape.*—Lower part is funnel-shaped, formed by 5 fused petals; corolla margin is salver-shaped, formed by the petals lobes opening outward.

*Size.*—Diameter (flower face): 7.3 cm. Depth (total length of flower): 4.6 cm. Funnel: Length: 3.3 cm. Diameter (at opening): About 1.5 cm. Outside texture: Weakly furrowed with glandular hair along the veins.

*Mature flower.*—Face/Margin Color: Upper surface: RHS N89A and later to RHS N88A, with RHS 186B weak, radial (mid-petal) veins. Lower surface: RHS N88B.

*Corolla.*—Shape of corolla: Tube-shaped. Color inside (throat): RHS N89A (deep-violet). Color outside: RHS N92D (dull-violet).

*Petals.*—Apex: Cuspidate. Base: Fused. Margin: Entire. Waviness: Weak to medium. Lobation: Moderate. Texture: Smooth and glabrous.

*Calyx.*—Composed of 5 sepals fused at the base.

*Sepals.*—Number: 5. Color: RHS 143A (for both upper and lower surfaces). Length: 1.5 cm to 1.6 cm. Width: 0.3 cm. Shape: Lanceolate. Apex: Acute. Base: Fused. Margin: Entire. Texture: Pubescent with rough hair.

Reproductive organs:

*Stamens.*—Number: 5. Filament color: RHS N155A (white). Filament length: 1.7 cm to 2.0 cm. Filament diameter: 0.1 cm. Pollen color: RHS 98D (bluish). Pollen amount: Moderate.

*Pistil.*—Number: 1. Length: 2.1 cm. Stigma color: RHS 145A. Style color: RHS 145D. Style length: 1.7 cm.

Fruit and seed set: No seed set observed so far.

Disease and insect resistance: No particular resistance or susceptibility has been observed.

COMPARISON WITH PARENTAL AND COMMERCIAL CULTIVARS

'Jam Bule' differs from the female parent 'Kakegawa S28' (U.S. Plant Pat. No. 13,887) by having blue flowers while 'Kakegawa S28' has purple flowers. In addition, 'Jam Bule' has a lower plant habit and more basal branching than 'Kakegawa S28'.

'Jam Bule' differs from the male parent 'PY152' (unpatented) by having deeper green foliage, richer flowering and more vigorous growth than 'PY152'.

'Jam Bule' differs from the commercial variety 'Whip Bule' (U.S. Plant Patent Applied for) by having larger flowers, longer leaves, shorter branches and a more compact plant habit than 'Whip Bule'.

'Jam Bule' differs from the commercial variety 'Surfinia Blue' (unpatented) by having a deeper bluish and less violet flower color than 'Surfinia Blue'. In addition, 'Jam Bule' has smaller flowers and leaves, develops more flowers, and has an earlier flowering response than 'Surfinia Blue'.

I claim:

1. A new and distinct cultivar of *petunia* plant as shown and described herein.

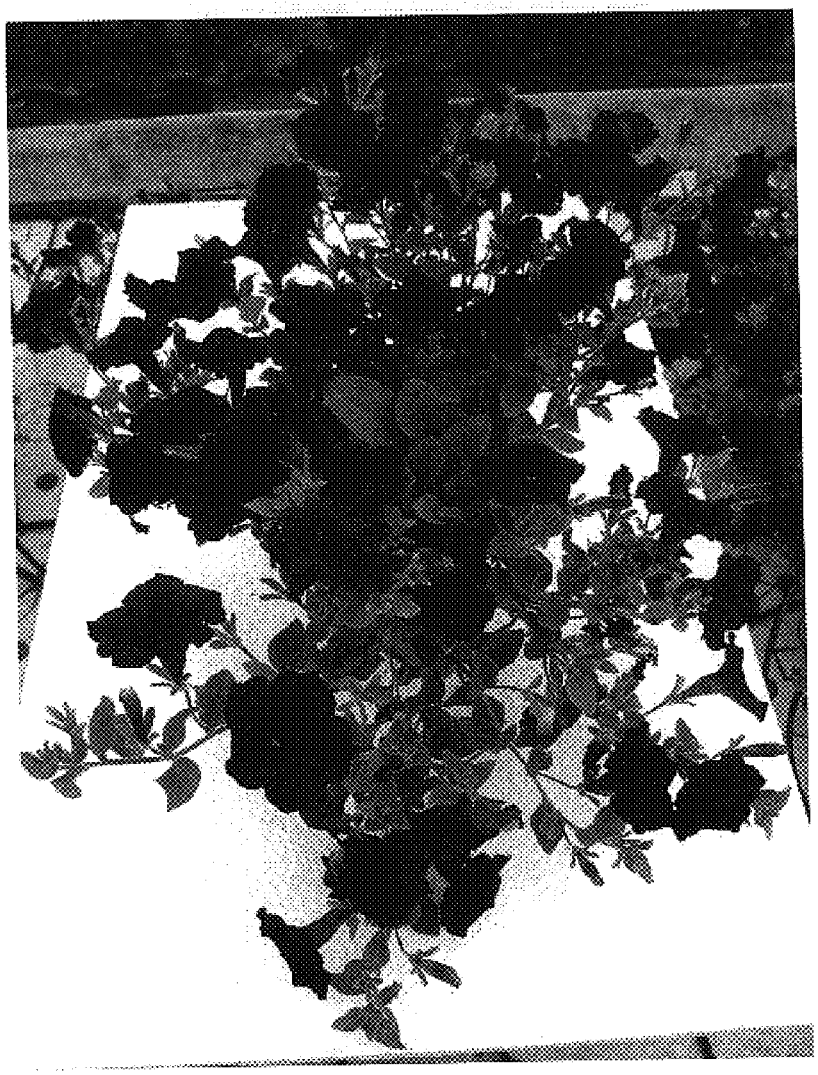

* * * * *